United States Patent [19]
Dahlen et al.

[11] 3,980,793
[45] Sept. 14, 1976

[54] CARBONATE ESTERS OF PENICILLINS AND COMPOSITIONS AND METHODS FOR TREATMENT OF BACTERIAL INFECTIONS

[75] Inventors: Sven Erik Dahlen, Huddinge; Bertil Ake Ekstrom; Berndt Olof Harald Sjoberg, both of Sodertalje, all of Sweden

[73] Assignee: Astra Lakemedel Aktiebolag, Sodertalje, Sweden

[22] Filed: Sept. 9, 1974

[21] Appl. No.: 504,177

Related U.S. Application Data

[63] Continuation-in-part of Ser. No. 337,720, March 2, 1973, abandoned.

[30] Foreign Application Priority Data

Mar. 13, 1972 United Kingdom............... 11687/72

[52] U.S. Cl............................... 424/271; 260/239.1
[51] Int. Cl.²........................................ A61K 31/43
[58] Field of Search................... 424/271; 260/239.1

[56] References Cited
UNITED STATES PATENTS

| | | | |
|---|---|---|---|
| 3,660,575 | 5/1972 | Fredeviksen et al................ | 424/271 |
| 3,697,507 | 10/1972 | Fredeviksen et al............. | 260/239.1 |

*Primary Examiner*—Jerome D. Goldberg
*Assistant Examiner*—Allen J. Robinson
*Attorney, Agent, or Firm*—Brumbaugh, Graves, Donohue & Raymond

[57] ABSTRACT

New carbonate esters of penicillins, having the formula

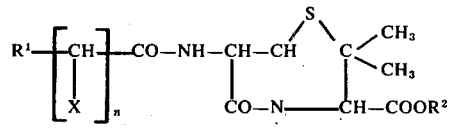

wherein $R^1$ is substituted or unsubstituted alkyl, alkenyl, aryl, aryloxy or heterocyclic group, $R^2$ is

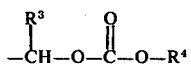

in which formula
$R^3$ is H or -CH$_3$,
$R^4$ is a substituted or unsubstituted alkyl, cycloalkyl, aryl, aralkyl or heterocyclic group, X is hydrogen, azido or hydroxy, n is 0 or 1, provided that X is hydroxy when n is 1 and $R^4$ is an unsubstituted alkyl group and $R^1$ is an alkyl, thienyl, furyl, phenyl or hydroxy-substituted phenyl group, useful as active ingredients of pharmaceutical preparations: processes for their preparation; and methods for the treatment of bacterial infections.

14 Claims, No Drawings

CARBONATE ESTERS OF PENICILLINS AND COMPOSITIONS AND METHODS FOR TREATMENT OF BACTERIAL INFECTIONS

This application is a continuation-in-part of copending U.S. Pat. application Ser. No. 337,720/73, filed Mar. 2, 1973, now abandoned.

The present invention relates to new penicillins and methods of their preparation. The invention also relates to the preparation of pharmaceutical preparations containing the penicillins and to methods for the pharmacological use of the penicillins. The invention relates in a further aspect to new intermediates useful in the preparation of the penicillins. More precisely this invention relates to carbonate esters of penicillins of the general formula

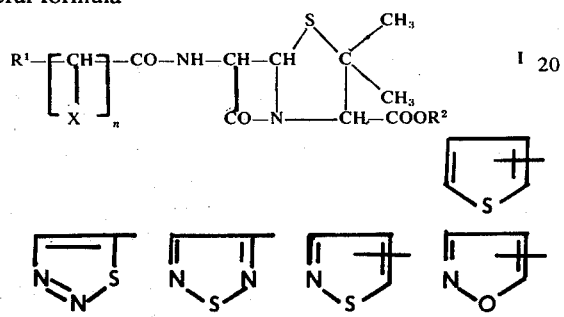

and therapeutically acceptable salts thereof in which formula $R^1$ is selected from the group consisting of alkyl and alkenyl groups containing from 1 to 10 carbon atoms, aryl groups such as phenyl and naphtyl, aryloxy groups such as phenoxy groups, and heterocyclic groups such as furyl, thienyl, pyrrolyl, pyridyl, pyrimidinyl, oxazolyl, isoxazolyl, thiazolyl, isothiazolyl, thiadiazolyl, tetrazolyl and sydnonyl groups, whereby the alkyl, alkenyl, aryl, aryloxy and heterocyclic groups may be unsubstituted or substituted with one or more members of the group consisting of amino groups, alkyl groups containing from 1 to 4 carbon atoms, alkoxy groups containing from 1 to 4 carbon atoms, hydroxy, halogen, alkylthio groups containing from 1 to 4 carbon atoms, carboxy, carboxymethyl, and phenyl $R^2$ is

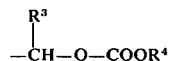

in which formula $R^3$ is selected from the group consisting of H and —$CH_3$;

$R^4$ is selected from the group consisting of alkyl groups containing from 1 to 8 carbon atoms, cycloalkyl groups containing from 3 to 7 carbon atoms, aryl and aralkyl groups, whereby the alkyl, cycloalkyl, aryl and aralkyl groups may be unsubstituted or substituted with one or more groups selected from the class consisting of azido groups, amino groups, substituted amino groups such as methylamino or diethylamino, nitro, and alkoxy groups containing from 1 to 4 carbon atoms;

X is selected from the group consisting of hydrogen, azido and hydroxy, and $n$ is 0 or 1, provided that X is hydroxy when $n$ is 1 and $R^4$ is an unsubstituted alkyl group, and $R^1$ is an alkyl, thienyl, furyl, phenyl or hydroxy-substituted phenyl group.

Illustrative examples of radicals included in the definitions given above are:

alkyl: methyl, ethyl, propyl, isopropyl, butyl, isobutyl, pentyl, hexyl, heptyl, octyl, 2-ethyl-hexyl cycloalkyl: cyclopropyl, cyclobutyl, cyclopentyl, cyclohexyl, cycloheptyl alkoxy: methoxy, ethoxy, propyloxy, isopropyloxy, butoxy, isobutoxy halogen: F, Cl, Br alkenyl: allyl, propenyl aryl: phenyl, naphtylmethyl aralkyl: benzyl, naphtylmethyl alkylthio: methylthio, ethylthio, butylthio Heterocyclic groups:

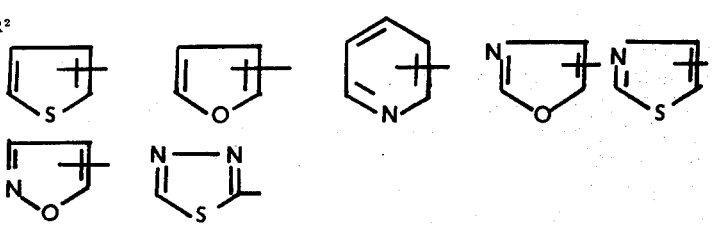

The above illustrative examples of radicals illustrate, where applicable, all the radicals mentioned above to the extent of the definition given to each radical and within the boundaries with regard to the number of carbon atoms which may be prescribed for each radical.

The compounds of the invention are of value in the treatment of infectious diseases in man or animal caused by bacterial organisms. They may be isolated and used as such but also, depending on the presence of basic or acidic groups in the molecule, in the form of salts with pharmaceutically acceptable organic or inorganic acids or bases. Examples of suitable acids are hydrochloric acid, hydrobromic acid, sulphuric acid, phosphoric acid, acetic acid, tartaric acid, citric acid, and fumaric acid. Examples of suitable bases are sodium hydroxide, potassium hydroxide, calcium hydroxide, aluminium hydroxide, ammonium hydroxide, non-toxic amines as trialkylamines, including triethylamine, procaine, dibenzylamine, N-benzyl-$\beta$-phenethylamine, 1-ephenamine, $N,N^1$-dibenzylethylenediamine, dehydroabiethylamino, $N,N^1$-bis-dehydroabiethylethylenediamine, N-(lower)-alkylpiperidine (e.g. N-ethyl-piperidine) and other bases which have been used for the preparation of salts with penicillins.

The side chain of the penicillin structure in formula I may contain an asymmetric center. Depending on the configuration around this center the compound will occur in two different diastereoisomeric forms which are both biologically active. Likewise the ester groups may contain asymmetric atoms giving rise to different diastereoisomeric forms which also all are biologically active. It is to be understood that the invention comprises the pure diastereoisomers as well as mixtures of them.

It is known that penicillins of the general structure (II):

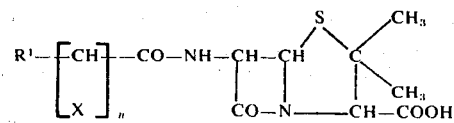

II or salts thereof, where n, $R^1$ and X are as defined above, have good antibacterial activity against grampositive and gramnegative bacteria and several such compounds have found extensive use in the clinic.

In combating bacterial infections it is desirable to have antibacterial agents that are well absorbed orally allowing an easy, convenient and safe treatment of the infection. Known penicillins of the formula II above are generally not completely absorbed from the gastrointestinal tract and many of the compounds very poorly so, owing to instability to the gastric juice or inherent properties and must be given by injection. It is one purpose of the present invention to provide chemical modifications of known penicillins of the formula II which are well absorbed orally and then rapidly hydrolyzed within the body to give blood and organ levels of the penicillins of the formula II that are higher than those levels which can be obtained at oral administration of the unmodified known penicillins of the formula II, as well as being adequate for the treatment of bacterial infections caused by bacteria being sensitive to such penicillins. To achieve the full antibacterial activity of the modified penicillins of the formula I it is necessary to choose such ester groups that are rapidly hydrolyzed in vivo under release of the known penicillins. It is an essential feature of the present invention to provide such ester groups that are rapidly hydrolyzed in the body after oral administration.

It is to be noted that the new carbonate esters of the present invention do not have any noticeable antibacterial activity themselves. However, their rapid absorption and hydrolysis results in high blood levels of known penicillins with known antibacterial activity. Accordingly, the carbonate esters of the present invention and the corresponding known penicillins can be used for the treatment of the same bacterial infections. The difference is that the carbonate esters of the present invention are more effective at oral administration, compared with oral administration of the corresponding unesterified penicillins. This unexpected property of the new carbonate esters is clearly demonstrated in Example 3, 4 and 12 of this specification.

The new carbonate esters having the formula I are well tolerated, give a low frequency of side-effects and may readily be used in pharmaceutical preparations, either as such or in the form of their salts, and they can be intermixed with solid carriers or adjuvants or both. In such preparations the ratio between the therapeutic substance and the carriers and adjuvants may vary between 1 % and 100 % (w/w), and may preferably vary between 1 % and 95 %. The preparation may either be processed to for instance tablets, pills or dragees or can be supplied to medical containers, such as capsules or as regards mixtures they can be filled on bottles. Pharmaceutically acceptable, organic or inorganic, solid or liquid carriers may be used, suitably for oral or enteral administration or for topical application, in manufacturing the preparations. Gelatine, lactose, starch, magnesium stearate, talc, vegetabilic and animalic fats and oils, vegetabilic rubber and polyalkylene glycol and other known carriers for pharmaceuticals are all suitable for manufacturing preparations of said compounds. Moreover the preparation may contain other pharmaceutically active components, being suitably administratable together with the compounds of the invention when treating infectious diseases for instance other suitable antibiotical substances, e.g. gentamycin and polymyxin.

In the treatment of bacterial infections in man, the compounds of invention are for example administered in amounts corresponding to 5 to 200 mg/kg/day, preferably in the range of 10 to 100 mg/kg/day in divided dosages, e.g. two, three or four times a day. They are administered in dosage units containing e.g. 175, 350, 500 and 1000 mg of the compounds.

The preferred compounds included in the formula I above are those compounds wherein the group

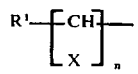

represents the side chain in known penicillins having strong antibacterial activity. Example of suitable meanings of the this group is ($R^1$ = aryl) benzyl, α-hydroxybenzyl, α-azidobenzyl, α-azido-m-fluorobenzyl, p-aminobenzyl and 2,6-dimethoxyphenyl; ($R^1$ = aryloxy) phenoxymethyl; ($R^1$ = heterocyclic) 3-pyridylmethyl, 2-phenyl-thiazolyl-4-methyl and 2-phenylthiadiazolyl-5-methyl.

A group of compounds, included in the formula I above, which has been especially exemplified in the working examples of this application is the group which can be represented by the general formula I in which $R^1$, $R^2$, $R^3$, X and n have the meaning given under the formula I and in which formula $R^4$ is selected from the group consisting of ethyl, benzyl and phenyl, which ethyl, benzyl and phenyl groups are unsubstituted or substituted with a group selected from amino, substituted amino such as diethylamino, azido, nitro or methoxy. Especially interesting groups of compounds with this restricted meaning of $R^4$ are formed when the group

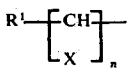

has anyone or all of the specific meanings illustrated in the foregoing paragraph, i.e. benzyl, α-hydroxybenzyl, α-azidobenzyl, α-azido-m-fluorobenzyl, p-aminobenzyl and 2,6-dimethoxyphenyl; phenoxymethyl; 3-pyridylmethyl, 2-phenylthiazolyl-4-methyl and 2-phenylthiadiazolyl-5-methyl.

Another group of preferred compounds within the formula I is the group formed when n=1 and $R^1$ is selected from a group consisting of γ-methylbutyl, 5-methyl-pentyl, n-hexyl, phenyl, 2- and 3-thienyl, 2- or 3 furyl, oxazolyl, thiazolyl, 2-phenyl-thiazolyl-2-, 3-pyridyl, m-fluorophenyl, p-hydroxy-phenyl, p-amino-phenyl-, phenoxy, n-heptyl, 1-butenyl, and X from a group consisting of hydrogen, azido and hydroxy and $R^2$ from a group consisting of lower alkoxycarbonyloxymethyl, 1'-lower alkoxycarbonyloxy-ethyl, phenoxycarbonyloxymethyl, and 1'-phenoxycarbonyloxy-ethyl, where the alkoxycarbonyloxy and aryloxycarbonyloxy groups in $R^2$ are substituted with amino, (lower)-alkylamino or di(lower)-alkylamino groups.

A further group of preferred compounds within the formula I is obtained when at the same time as n=0, $R^1$ is selected from a group consisting of n-butyl, Δ$^2$-pentenyl, alkylthiomethyl, 2,6-dimethoxyphenyl, 2-methoxy- 6-chlorophenyl, 2-biphenyl and 2-ethoxynaphtyl, and R² from a group consisting of lower alkoxycarbonyloxymethyl, 1'-lower alkoxycarbonyloxy-ethyl, phenoxycarbonyloxymethyl, 1'-phenoxycarbonyloxy-ethyl, where the alkoxycarbonyloxy and aryloxycarbonyloxy groups in R² may be substituted with amino, (lower)alkylamino or di(lower)alkylamino groups.

Examples of preferred compounds of the invention are collected in Table 1.

Table 1.

Preferred compounds of the invention $$R^1 \left[ \begin{array}{c} -CH- \\ | \\ X \end{array} \right]_n -CO-NH-CH-CH \begin{array}{c} S \\ \diagdown \\ C \end{array} \begin{array}{c} CH_3 \\ \diagdown \\ CH_3 \end{array}$$
$$\hspace{5cm} CO-N\text{———}CH-COOR^2$$

| R¹ | X | n | R² |
|---|---|---|---|
| (CH₃)₂CH—CH₂ | H | 1 | —CH₂OCOOCH₂CH₂NH₂ |
| (CH₃)₂—CH—(CH₂)₂— | H | 1 | —CH₂OCOOCH₂CH₂—NH—CH₃ |
| CH₃—(CH₂)₅— | H | 1 | —CH₂OCOOCH₂CH₂N(C₂H₅)₂ |
| CH₃—CH₂—CH=CH— | H | 1 | —CH₂OCOOC₆H₅ |
| HOOC—CH(NH₂)—(CH₂)₂— | H | 1 | —CH₂OCOOC₂H₅ |
| C₆H₅— | | 0 | —CH₂OCOOC₂H₅ |
| 2,6-di-OCH₃—C₆H₃— | | 0 | —CH₂OCOOC₂H₅ |
| 2,6-di-OCH₃—C₆H₃— | | 0 | —CH(CH₃)—OCOOC₂H₅ |
| 2,6-di-OCH₃—C₆H₃— | | 0 | —CH₂—OCOOCH₂CH₂NH₂ |
| 2,6-di-OCH₃—C₆H₃— | | 0 | —CH(CH₃)—OCOOCH₂—NH₂ |
| 2-ethoxy-naphtyl- | | 0 | —CH₂OCOOCH₃ |
| 2-ethoxy-naphtyl | | 0 | —CH₂—OCOOC₂H₅ |
| 2-ethoxy-naphtyl- | | 0 | —CH₂—OCOOC₄H₉ |
| 2-ethoxy-naphtyl- | | 0 | —CH₂—O—COOCH₂CH₂NH₂ |
| 2-biphenyl- | | 0 | —CH₂—OCOOC₂H₅ |
| 2-biphenyl- | | 0 | —CH₂—OCOOCH₂CH₂NH₂ |
| 2-biphenyl- | | 0 | —CH(CH₃)—OCOOCH₂—NH₂ |
| 2-biphenyl- | | 0 | —CH(CH₃)—OCOOC₂H₅ |
| C₆H₅— | H | 1 | —CH₂OCOOCH₂CH₂NH₂ |
| " | " | 1 | —CH₂OCOOCH₂CH₂NH—CH₃ |
| " | " | 1 | —CH₂OCOOCH₂CH₂—N(C₂H₅)₂ |
| " | " | 1 | —CH₂OCOOC₆H₅ |
| " | " | 1 | —CH₂OCOO—(indanyl) |
| " | " | 1 | —CH(CH₃)—OCOOCH₂CH₂NH₂ |
| " | " | 1 | —CH(CH₃)—OCOO—(cyclopentyl) |
| p-H₂N—C₆H₄— | " | 1 | —CH₂—OCOOC₂H₅ |
| " | " | 1 | —CH(CH₃)—OCOOC₂H₅ |
| p-F—C₆H₄ | H | 1 | —CH₂OCOOCH₂CH₂NH₂ |
| (thiazolyl) | H | 1 | —CH₂OCOOC₂H₅ |

Table 1.-continued

Preferred compounds of the invention $$R^1-[CH(X)]_n-CO-NH-CH-CH(S-C(CH_3)_2-CH(COOR^2)-N-CO)$$

| R¹ | X | n | R² |
|---|---|---|---|
| C₆H₅—(2,5-thiazolyl) | H | 1 | —CH₂OCOOC₂H₅ |
| '' | H | 1 | —CH₂OCOOCH₂CH₂NH—CH₃ |
| '' | H | 1 | —CH(CH₃)—OCOOCH₂NH₂ |
| '' | H | 1 | —CH(CH₃)—OCOOCH₂CH₂NH₂ |
| C₆H₅—(2,5-thiadiazolyl) | H | 1 | —CH₂OCOOC₂H₅ |
| '' | H | 1 | —CH(CH₃)—OCOOC₆H₅ |
| 3-pyridyl | H | 1 | —CH₂OCOOC₂H₅ |
| '' | H | 1 | —CH(CH₃)—OCOOC₂H₅ |
| '' | H | 1 | —CH₂—OCOOCH₂CH₂NH₂ |
| '' | H | 1 | —CH(CH₃)—OCOOC₆H₅ |
| F—(5-fluoro-3-pyridyl) | H | 1 | —CH₂—OCOOC₂H₅ |
| '' | H | 1 | —CH₂OCOOCH₂CH₂NH₂ |
| '' | H | 1 | —CH(CH₃)—OCOOC₂H₅ |
| '' | H | 1 | —CH₂OCOO(CH₂)₆CH₃ |
| C₆H₅— | N₃ | 1 | —CH₂OCOOCH₂CH₂N(C₂H₅)₂ |
| '' | N₃ | 1 | —CH₂OCOO—C₆H₅ |
| '' | N₃ | 1 | —CH₂OCOO—(indanyl) |
| '' | N₃ | 1 | —CH₂—O—COO—C₆H₄—OCH₃ |

Table 1.-continued

Preferred compounds of the invention $$R^1-[CH-X]_n-CO-NH-CH-CH\underset{CO-N-CH-COOR^2}{\overset{S}{\diagdown}}C\underset{CH_3}{\overset{CH_3}{\diagup}}$$

| R¹ | X | n | R² |
|---|---|---|---|
| " | N₃ | 1 | $-\underset{CH_3}{\overset{\|}{CH}}-O-COOC_6H_5$ |
| F—⟨phenyl⟩— | N₃ | 1 | $-CH_2OCOOCH_2-N(C_2H_5)_2$ |
| F—⟨phenyl⟩— | N₃ | 1 | —CH₂—OCOOC₆H₅ |
| " | N₃ | 1 | —CH₂OCOO—⟨phenyl⟩—OCH₃ |
| " | N₃ | 1 | —CH₂OCOO—⟨indanyl⟩ |
| " | N₃ | 1 | —CH₂—OCOOCH₂CH₂NH₂ |
| ⟨thienyl⟩ | N₃ | 1 | $-CH_2OCOOCH_2CH_2N(C_2H_5)_2$ |
| (CH₃)₂CH—CH₂— | N₃ | 1 | $-CH_2OCOOCH_2CH_2N(C_2H_5)_2$ |
| C₆H₅— | OH | 1 | —CH₂—OCOOC₂H₅ |
| " | OH | 1 | —CH₂OCOOCH₂CH₂NH₂ |
| " | OH | 1 | —CH₂OCOOCH₂CH₂—NHCH₃ |
| " | OH | 1 | —CH₂—OCOOC₆H₅ |
| " | OH | 1 | —CH₂—OCOO—⟨indanyl⟩ |
| " | OH | 1 | —CH₂—OCOOC₅H₁₁ |
| " | OH | 1 | $-\underset{CH_3}{\overset{\|}{CH}}-OCOOC_2H_5$ |
| " | OH | 1 | $-\underset{CH_3}{\overset{\|}{CH}}-OCOOC_3H_7$ |
| Cl—⟨phenyl⟩— | OH | 1 | —CH₂OCOOC₂H₅ |
| C₆H₅O— | H | 1 | —CH₂—OCOOC₂H₅ |
| " | H | 1 | —CH₂OCOOCH₂CH₂NH₂ |

The compounds of the invention may be prepared according to different methods.

Method A

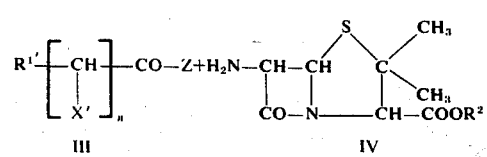

$$R^1-[CH-X']_n-CO-Z + H_2N-CH-CH\underset{CO-N-CH-COOR^2}{\overset{S}{\diagdown}}C\underset{CH_3}{\overset{CH_3}{\diagup}}$$

III          IV

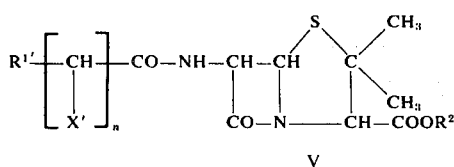

V

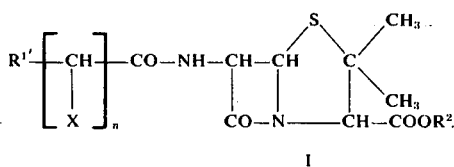

I

According to this method an activated carboxylic acid derivative III where $R^{1'}$ is $R^1$, defined above, or when $R^1$ contains an amino, carboxy or hydroxy group a protected derivative of $R^1$, and X' is either X, defined above, or in case X contains an amino or hydroxy group a protected derivative of X, and —CO-Z is a reactive group capable of reacting with an amino group under formation of an amide moiety, e.g. an acid chloride or its functional equivalent, is brought to react with an ester of 6-aminopenicillanic acid (IV) where $R^2$ is as defined above, under formation of a penicillin ester V.

When $R^{1'} = R^1$ and X' = X the product is a compound of the invention. When $R^1$ or X' contain amino, carboxy or hydroxy groups that are protected, the protecting group is removed in per se known manner in at least one additional step to give the compounds of the general formula I. As protecting groups for the amino and hydroxy groups such protecting groups can be used that can be removed without destruction of the penicillin ring system. Such protecting groups known to the art are e.g. the benzyloxy carbonyl, the o-nitrophenylsulfenyl, the 2-p-tolylsulphonyl-ethoxy-carbonyl, the β-trichloroethoxycarbonyl and the 1-methoxycarbonylpropen-2-yl group as protecting groups for the amino groups, e.g. the benzyl group as protecting group for the hydroxy group and the benzyl, β-trichloroethyl, 2,6-dichlorobenzyl and the 2-p-tolylsulphonyl-ethyl group as protecting group for the carboxy group.

The reaction between the compounds of the formula III and IV constitutes an acylation of an ester of 6-aminopenicillanic acid and can be performed in the manner described for acylation of other esters of 6-aminopenicillanic acid (e.g. in French Pat. No. 1 576 027). The acylating group —CO—Z in the compound III may be an acid chloride group, or a group functioning in the same way, e.g. an acid bromide, an acid azide, an anhydride, a mixed anhydride formed with an inorganic acid or an organic acid and especially with an alkoxyformic acid.

The compound III may also be a derivative obtained by reaction between a compound of the formula

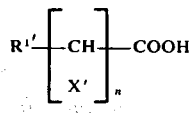

wherein n, $R^{1'}$ and X' have the meanings specified above, and a carbodiimide or other compounds functioning in the same way such as N,N¹- carbonyl-diimidazole, N-ethyl-5-phenylisoxazolium-3'-sulphonate or N-tert.butyl-5-methylisoxazolium perchlorate.

The reaction can be performed in organic solvents like diethylether, tetrahydrofurane, acetone, ethyl acetate, chloroform, methylene chloride, dimethylformamide, dimethyl sulfoxide, or hexamethylphosphoramide, in water or in aqueous organic solvents in presence of organic or inorganic bases like triethylamine, quinoline, pyridine, N-methyl-morpholine, sodium hydroxide, sodium bicarbonate or potassium carbonate.

The compound of the general formula V may be isolated by extraction from the reaction mixture, if necessary after dilution with water and neutralization.

The esters of 6-aminopenicillanic acid with the general structure IV may be prepared by treatment of salts of 6-APA with compounds $R^1$—$Y^1$, where $R^2$ has the same meaning as above and $Y^1$ is halogen or a functionally equivalent group capable of reacting with a carboxy group under formation of an ester linkage, such as an organic sulphonic acid residue. The reaction is preferably performed in organic solvents like dimethylformamide, dimethylsulphoxide or hexamethylphosphoramide.

Alternatively salts of 6-acylaminopenicillanic acids with acyl groups that can be removed without destruction of the penicillin ring system are treated with $R^2$—$Y^1$ to give esters from which the acyl groups then are removed to give the esters of 6-aminopenicillanic acid of the formula IV. One preferred method consists of reacting a salt, e.g. a sodium, potassium or tetraalkylammonium salt of benzylpenicillin, with $R^1$—$Y^1$ in an organic solvent like acetone, dimethylformamide, dimethylsulphoxide, hexamethylphosphoramide, methylethylketon, chloroform, methylenechloride or in a mixture of an organic solvent and water, e.g. aqueous acetone or dioxane to give the corresponding ester of benzylpenicillin. The phenylacetyl side chain is then removed according to the method described in Neth. Pat. Publ. 6 401 421 or South African Pat. Publ. 67/2927 by treatment with phosphorus pentachloride in presence of a tertiary organic base to give an imino chloride which is reacted with an alcohol like propanol to give the corresponding imino ether which is hydrolyzed by addition of water or alcoholized by addition of alcohol to give the ester III. Alternatively the phenylacetyl side chain may be removed by enzymatic hydrolysis using an E.coli acylase according to method described in French Patent 1 576 027.

In still another method N-protected 6-aminopenicillanic acids are reacted with $R^2$—$Y^1$ to give the corresponding ester from which the protecting groups are removed to give the compounds of the general formula IV. Examples of protecting groups which can be used are the benzyloxycarbonyl groups which is removed by catalytic hydrogenation, the o-nitrophenylsulphenyl group which can be removed by treatment with nucleophilic agents at acid pH (Jap.Pat. 505 176) and the trityl group which can be removed by mild acid hydrolysis.

Method B

A natural penicillin of the formula

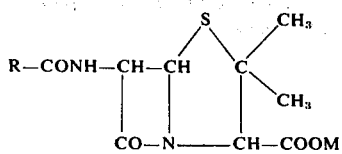

VI where RCO represents the acyl group in the side chain of the natural penicillin and M represents hydrogen or an alcali metal atom such as sodium, potassium, calcium, is esterified by reaction with a compound of the formula $$R^2-Y^1 \qquad \text{VII}$$

where $R^2$ and $Y^1$ have the meanings specified above, whereafter the ester of the formula

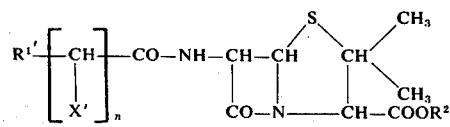
VIII thus formed is reacted with a phosphorous halide in an inert solvent and suitably in presence of a tertiary amine to give an imino halide compound, which is reacted with a lower alcohol to give an iminoether derivative, which imino ether thereafter is reacted with a compound of the formula

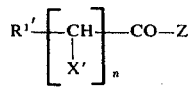
III wherein $R^{1'}$, $X'$ and $Z$ have the meanings specified above, and the reaction product treated with water or an alcohol to give a compound of the formula

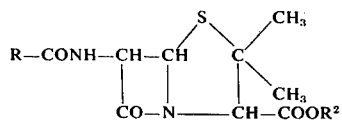
V which compound thereafter is converted to a compound of the formula I as is described under A above. In this method the intermediate imino ether compound is directly acylated without isolation of any intermediate products.

The group RCO- in the compound of the formula VI is an organic acyl group contained in known natural penicillins. Thus the group R may be an alkyl, cycloalkyl, aryl, aralkyl or heterocyclic group and derivatives thereof. Examples of suitable groups R are heptyl, phenoxymethyl, 2-thienylmethyl, 2-furylmethyl, and benzyl. Examples of suitable phosphorous halides are phosphorous pentachloride, phosphorous pentabromide, phosphorous oxychloride, phosphorous trichloride, etc. Phosphorous pentachloride is preferred. Examples of suitable alcohols with which the imino halide may be treated are lower alkyl alcohols such as methanol, ethanol, and n-propanol.

Method C

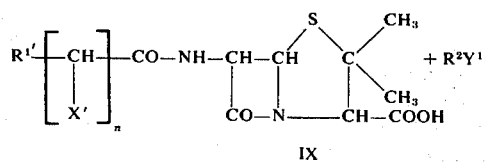
IX

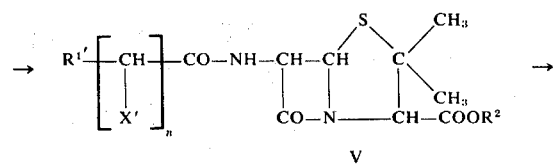
V

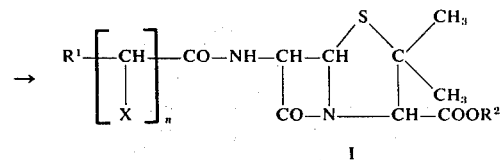
I

Penicillins with the formula IX, where $R^{1'}$ and $X'$ and n are as defined above, are prepared by acylation of 6-aminopenicillanic acid according to known methods. Treatment of the penicillins with the formula IX with a compound of the formula $$R^2-Y^1$$

where $R^2$ is as defined above and $Y^1$ is halogen, preferably chlorine, bromine or iodine, or an organic sulphonic acid residue, gives the compounds of formula V, which as described in method A are converted into compounds of the invention (I).

The reaction is preferably performed with a salt, e.g. a sodium, potassium, calcium, tetraalkylammonium or a trialkylammonium salt of the compound IX in an organic solvent like acetone, tetrahydrofurane, chloroform, methylene chloride, dimethylformamide, dimethylsulphoxide or hexamethylphosphoramide or in a mixture of water and an organic solvent, e.g. aqueous dioxane or acetone.

As described above the starting material may be in the form of a salt, for instance a sodium, potassium, calcium or trialkylammonium salt, in some of the ways for the preparation of the compounds of the invention.

In addition, tetraalkylammonium salts and other analogues salts such as salts where the cation has the formula $$A^1A^2A^3A^4N^+$$

in which formula $A^1$ is selected from the group consisting of straight and branched alkyl groups containing from 3 to 6 carbon atoms, substituted and unsubstituted aryl, and substituted and unsubstituted aralkyl, and wherein $A^2$, $A^3$ and $A^4$, which are the same or different, are selected from the group consisting of straight and branched alkyl groups containing from 1 to 6 carbon atoms, provided that $A^2$, $A^3$ and $A^4$ are alkyl with 3–6 carbon atoms when $A^1$ is alkyl, may be used.

Illustrative examples of suitable combinations of $A^1$, $A^2$, $A^3$ and $A^4$ in the quaternary ammonium ion $A^1A^2A^3A^4N^+$ are given below:

Table I.

Examples of suitable combinations of the radicals $A^1$–$A^4$ in the $A^1A^2A^3A^4N^+$ ion

| $A^1$ | $A^2$ | $A^3$ | $A^4$ |
|---|---|---|---|
| n-propyl | n-propyl | n-propyl | n-propyl |
| i-propyl | i-propyl | i-propyl | i-propyl |
| n-butyl | n-butyl | n-butyl | n-butyl |
| i-butyl | i-butyl | i-butyl | i-butyl |
| n-pentyl | n-pentyl | n-pentyl | n-pentyl |
| n-hexyl | n-hexyl | n-hexyl | n-hexyl |

Table I.-continued

| Examples of suitable combinations of the radicals $A^1$–$A^4$ in the $A^1A^2A^3A^4N^+$ ion | | | |
|---|---|---|---|
| $A^1$ | $A^2$ | $A^3$ | $A^4$ |
| phenyl | methyl | methyl | methyl |
| phenyl | ethyl | ethyl | ethyl |
| p-tolyl | ethyl | ethyl | ethyl |
| p-chlorophenyl | ethyl | ethyl | ethyl |

When the radicals $A^1$–$A^4$ all are different the resulting ion contains an asymmetric centre and may occur in two enantiomeric forms. Epimeric forms can occur if $A^1$, $A^2$, $A^3$ and/or $A^4$ contain one or more asymmetric carbon atoms.

Examples of quaternary ammonium ions containing an asymmetric centre are given in Table II below:

Table II.

| Examples of quaternary ammonium ion $A^1A^2A^3A^4N^+$ containing an asymmetric centre | | | |
|---|---|---|---|
| $A^1$ | $A^2$ | $A^3$ | $A^4$ |
| benzyl | n-propyl | i-propyl | n-butyl |
| benzyl | n-propyl | i-propyl | sec.butyl |
| benzyl | n-propyl | n-butyl | sec.butyl |
| n-propyl | n-propyl | n-butyl | sec.butyl |
| n-propyl | n-propyl | n-propyl | sec.butyl |
| n-propyl | n-propyl | n-propyl | sec.pentyl |
| n-propyl | n-propyl | n-propyl | sec.hexyl |
| n-propyl | n-propyl | n-butyl | sec.hexyl |

The use as described above of a quaternary salt form of the starting material for the preparation of the compounds of this invention is not previously described in the literature pertaining to this technical field. In this method the preferred cation is the tetraalkylammonium ion, particularly the tetrabutylammonium ion. The preferred solvents are chloroform, methylenechloride and acetone.

The quaternary ammonium salt form of the above described starting material may be prepared by reacting the starting material in question with a quaternary ammonium salt of the formula

$$A^1A^2A^3A^4N^+ \; B^-$$

wherein $A^1$, $A^2$, $A^3$ and $A^4$ have the meanings specified above and B is a suitable anion such as $HSO_4^-$, $CL^-$ or $CH_3COO^-$ to the formation of a quaternary salt of the starting material.

The salts of the formula above which contains B as the anion may be prepared in known manner analogous as described in for instance Belgian patent 751 791. The anion $B^-$ is in the preferred embodiment $HSO_4^-$.

The following examples will further illustrate the invention.

EXAMPLE 1.

p-nitro-benzyloxycarbonyloxymethylbenzylpenicillinate

To a stirred cooled suspension of potassium benzylpenicillinate (7.45 g, 0.02 mole) in dimethyl sulphoxide (10 ml) was added a solution of p-nitrobenzylchloromethyl carbonate (4.9 g, 0.02 mole) in dimethylsulphoxide (8 ml), during 30 minutes. After stirring at room temperature for 20 hours the mixture was poured into 60 ml of saturated sodium bicarbonate solution and extracted with 40+5+5 ml of ethylacetate. The combined organic extracts were washed with diluted sodium bicarbonate, water and brine, dried and evaporated in vacuo at 30°C to give 9.0 g of a reddish heavy oil. The product was purified by column chromatography to give a pale yellow solid (5.4 g). The product showed strong IR absorbtion at 1785–1750 $cm^{-1}$ due to $\beta$-lactam and ester carbonyls. The product showed a purity of 92,0 % (iodometric) and was rapidly hydrolyzed in presence of human serum. NMR ($CDCl_3$, tetramethylsilane as internal standard) = 1.45 (s), 3.63 (s), 4.45 (s), 5.35 (s), 5.50–5.80 (m), 5.85 (s), 6.30–6.50 (d), 7.35 (s), 7.50–8.40 (m) ppm.

EXAMPLE 2.

p-nitro-benzyloxycarbonyloxymethyl-$\alpha$-hydroxybenzylpenicillinate

To a stirred cooled suspension of sodium $\alpha$-hydroxybenzylpenicillinate (3.7 g, 0.01 mole) in dimethylsulphoxide (10 ml) was added a solution of p-nitrobenzylchloromethylcarbonate (2.5 g, 0.01 mole) in dimethylsulphoxide (10 ml) during 30 minutes. After stirring at room temperature for 20 hours the mixture was poured into 60 ml of saturated sodium bicarbonate solution and extracted with 40+5+5 ml of ethylacetate. The combined organic extracts were washed with dilute sodium bicarbonate, water and brine, dried and evaporated in vacuo at 30°C to give 4.3 g of a reddish oil. The product was purified with column chromatography to give title product as a pale yellow solid (1.6 g). The product showed strong IR absorbtion at 1785–1750 $cm^{-1}$ due to $\beta$-lactam and ester carbonyls.

The product showed a purity of 96.3 % (iodometric) and was rapidly hydrolyzed in presence of human serum. NMR ($CDCl_3$, tetramethylsilane as internal standard) = 1.45 (s), 1.60 (s), 4.45 (s), 5.08 (s), 5.35 (s), 5.50–5.80 (m), 5.90 (s), 7.43 (s), 7.50–8.40 (m) ppm.

EXAMPLE 3.

Ethoxycarbonyloxymethyl-phenoxymethylpenicillinate

To a stirred cooled suspension of potassium phenoxymethyl-penicillinate (11.6 g, 0.03 mole) in dimethylsulphoxide (12 ml) was added ethylchloromethylcarbonate (4.6 g, 0.03 mole), during 30 minutes. After stirring at room temperature for 16 hours the mixture was poured into 50 ml of saturated sodium bicarbonate solution and extracted with 3×50 ml of ethylacetate. The combined organic extracts were washed with dilute sodium bicarbonate, water and brine, dried and evaporated in vacuo at 30°C, repeatedly washed with petroleum ether, dissolved in ethylacetate and once more evaporated at 30°C to give title product as 4.4 g of a brownish oil. The product showed strong IR absorbtion at 1785–1750 $cm^{-1}$ due to $\beta$-lactam and ester carbonyls.

The product was rapidly hydrolyzed in presence of human serum. NMR ($CDCl_3$, tetramethylsilane as internal standard) = 1.15–1.45 (t), 1.55 (s), 1.60 (s), 4.10–4.45 (q), 4.50 (s), 4.55 (s), 5.50–5.80 (m), 5.85 (s), 6.80–7.50 (m) ppm.

Oral administration in mice of the product resulted in blood concentration peak level of 17.3 $\mu$g/ml of phenoxymethylpenicillin after 60 min. compared to blood concentration peak level of 15.9 $\mu$g/ml 30 minutes after a demonstration of equimolar amounts of potassium phenoxymethylpenicillinate.

EXAMPLE 4.

Ethoxycarbonyloxymethyl-2,6-dimethoxyphenyl-penicillinate

To a stirred cooled suspension of sodium-2,6-dimethoxyphenylpenicillinate (12.1 g, 0.03 mole) in dimethylsulphoxide (12 ml) was added ethylchloromethylcarbonate (4.6 g, 0.03 mole) during 30 min. After stirring at room temperature for 16 hours the mixture was poured into 50 ml of saturated sodium bicarbonate solution and extracted with 3×50 ml of ethylacetate. The combined organic extracts were washed with dilute sodium bicarbonate, water and brine, dried and evaporated in vacuo at 30°C to give title product as 12.8 g of pale yellow oil, which crystallized when treated with isopropylalcohol. M.p. 97.0–98.0°C. The product showed strong IR absorbtion at 1785–1750 $cm^{-1}$ due to $\beta$-lactam and ester carbonyls. The product was rapidly hydrolysed in presence of human serum. NMR ($CDCl_3$, tetramethylsilane as internal standard)=1.20–1.45 (t), 1.55 (s), 1.65 (s), 3.85 (s), 4.10–4.45 (q), 4.50 (s), 6.60–6.15 (m), 6.50–6.75 (m), 7.20–7.50 (m) ppm.

Oral administration in mice of the product resulted in blood concentration peak levels of 5.6 $\mu$g/ml of 2,6-dimethoxyphenylpenicillin after 60 minutes compared to blood concentration peak level of 2.6 $\mu$g/ml 60 minutes after oral administration of equimolar amounts of sodium 2,6-dimethoxyphenylpenicillinate.

EXAMPLE 5.

Ethoxycarbonyloxymethyl 6-(3-pyridylacetamido) penicillinate hydrochloride

To a stirred cooled suspension of 6-(3-pyridylacetamido)penicillanic acid (3.35 g, 0.01 mole) in dimethylsulphoxide (5 ml) was added dropwise ethylchloromethylcarbonate (1.4 g, 0.01 mole). After stirring at room temperature for 16 hours the mixture was poured into 25 ml of saturated sodium bicarbonate solution and extracted with 3×25 ml of ethylacetate. The combined organic extracts were washed with 3×25 ml of sodium bicarbonate and 25 ml of water. The organic solution was then extracted with 2×25 ml of water, acidified with dilute hydrochloric acid to pH=3.0. The combined water extracts were washed with diisopropylether and freeze-dried to afford 1.0 g of title product. The product showed strong IR absorbtion at 1780–1750 $cm^{-1}$ due to $\beta$-lactam and ester carbonyls. The product was rapidly hydrolyzed in presence of human serum.

EXAMPLE 6.

1'-Ethoxycarbonyloxyethyl 6-(3-pyridylacetamido) penicillinate hydrochloride

In the same way as in example 5, title product was synthesized from 6-(3-pyridylacetamido)penicillanic acid (3.35 g, 0.01 mole) and ethyl-$\alpha$-chloroethyl-carbonate (1.5 g, 0.01 mole) in 5 ml of dimethylsulphoxide. The freeze-dried product (0.1 g) showed strong IR absorbtion at 1780–1750 $cm^{-1}$ due to $\beta$-lactam and ester carbonyls. The product was rapidly hydrolyzed in presence of human serum.

EXAMPLE 7.

1'-Phenoxycarbonyloxyethyl 6-(3-pyridylacetamido) penicillinate hydrochloride

In the same way as in example 5, title product was synthesized from 6-(3-pyridylacetamido)penicillanic acid (2.2 g, 0.007 mole) and phenyl-chloroethylcarbonate (1.5 g, 0.007 mole) in 5 ml of dimethylsulphoxide. The freeze-dried product (0.2 g) showed strong IR absorbtion at 1780–1750 $cm^{-1}$ due to $\beta$-lactam and ester carbonyls. The product was rapidly hydrolyzed in presence of human serum.

EXAMPLE 8.

Ethoxycarbonyloxymethyl-6-caprylamidopenicillinate

In the same way as in example 3, title product was synthesized from sodium 6-caprylamidopenicillinate (3.6 g, 0.01 mole) and ethylchloromethylcarbonate (1.5 g, 0.01 mole) in 5 ml of dimethylsulphoxide. Title product was obtained as 1.9 g of a yellow oil. The product showed strong IR absorbtion at 1780–1750 $cm^{-1}$ due to $\beta$-lactam and ester carbonyls. The product was rapidly hydrolyzed in presence of human serum.

EXAMPLE 9.

Ethoxycarbonyloxymethyl-6-(2-phenylthiadiazolyl-5-acetamido)-penicillinate

In the same way as in example 3, title product was synthesized from potassium 6-(2-phenylthiadiazolyl-5-acetamido)-penicillinate (2.3 g, 0.005 mole) and ethylchloromethylcarbonate (1.5 g, 0.01 mole) in 5 ml of dimethylsulphoxide. The organic extract was washed with acidic water, dried and evaporated in vacuo at 30°C, washed repeatedly with petroleum ether, dissolved and evaporated to give 1.2 g of title product as a brownish gum. The product showed strong IR absorbtion at 1780–1750 $cm^{-1}$ due to $\beta$-lactam and ester carbonyls. NMR ($CDCl_3$, tetramethylsilane as internal standard) = 1.15–1.45 (t), 1.50–1.60 (d), 4.10–4.45 (q), 4.25 (s), 4.50 (s), 5.55–5.85 (m), 7.20–8.10 (m) ppm.

EXAMPLE 10.

1'-Phenoxycarbonyloxyethyl-6-(2-phenylthiadiazolyl-5-acetamido)-penicillinate

In the same way as in example 3 title product was synthesized from potassium 6-(2-phenylthiadiazolyl-5-acetamido)-penicillinate (4.6 g, 0.01 mole) and phenyl-$\alpha$-chloroethyl-carbonate (2.0 g, 0.91 mole) in 10 ml of dimethylsulphoxide. The reaction mixture was poured into 50 ml of ice cold sodiumbicarbonate solution and extracted with 3×50 ml of ether. The combined ether extracts were washed with sodium bicarbonate solution, water and brine, dried and evaporated in vacuo at 30°C, repeatedly washed with petroleum ether, dissolved and evaporated to give title product as a brownish oil (1.2 g). The product showed strong IR absorbtion at 1780–1750 $cm^{-1}$ due to $\beta$-lactam and ester carbonyls.

EXAMPLE 11.

Ethoxycarbonyloxymethyl-6-(2-phenylthiazolyl-4-acetamido)penicillinate

In the same way as in example 9, title product was synthesized from potassium 6-(2-phenylthiazolyl-4-acetamido)penicillinate (4.5 g, 0.01 mole) and ethylchloromethylcarbonate (2.8 g, 0.02 mole) in 10 ml of dimethylsulphoxide. The product was obtained as 2.7 g of a brownish solid foam. The product showed strong IR absorbtion at 1780–1750 $cm^{-1}$ due to $\beta$-lactam and ester carbonyls. The product was rapidly hydrolyzed in presence of human serum. NMR ($CDCl_3$, tetramethylsilane as internal standard) = 1.10–1.70 (m), 3.77 (s), 4.05–4.45 (q), 4.40 (s), 5.40–5.90 (m), 7.10–8.10 (m).

EXAMPLE 12.

1'-Ethoxycarbonyloxyethyl-α-hydroxy benzylpenicillinate

In the same way as in example 3, title product was synthesized from sodium α-hydroxybenzylpenicillinate (3.7 g, 0.01 mole) and ethyl-α-chloroethylcarbonate (3.0 g, 0.02 mole) in 25 ml of dimethylsulphoxide. The product was obtained as 4.2 g of a brownish foam. The product showed strong IR absorbtion at 1780–1750 cm$^{-1}$ due to β-lactam and ester carbonyls. The product was rapidly hydrolyzed in presence of human serum. NMR (CDCl$_3$, tetramethylsilane as internal standard) = 1.10–1.45 (t), 1.50–1.55 (d), 4.07–4.45 (q), 4.50 (s), 5.10 (s), 5.45–5.70 (m), 6.65–6.95 (q), 7.30–7.40 (s).

Oral administration in mice of the product resulted in blood concentration peak level of 16.3 μg/ml of α-hydroxybenzylpenicillinate after 45 minutes compared to blood concentration peak level of 9.6 μg/ml 120 minutes after administration of equimolar amounts of sodium α-hydroxybenzylpenicillinate.

EXAMPLE 13.

2-Ethylhexoxycarbonyloxymethyl-α-hydroxybenzyl-penicillinate

In the same way as in example 3, title product was synthesized from sodium α-hydroxybenzylpenicillinate (3.7 g, 0.01 mole) and 2-ethylhexylchloromethylcarbonate (2.2 g, 0.01 mole) in 10 ml of dimethylsulphoxide. The product was obtained as 3.7 g of a yellowish oil. The product showed strong IR absorbtion at 1780–1750 cm$^{-1}$ due to β-lactam and ester carbonyls. The product was rapidly hydrolyzed in presence of human serum. NMR (CDCl$_3$, tetramethylsilane as internal standard) = 0.80–1.70 (m), 4.00–4.40 (m), 4.45 (s), 5.05 (s), 5.50–5.90 (m), 7.30–7.45 (s).

EXAMPLE 14.

p-Nitrophenoxycarbonyloxy-methyl-benzylpenicillinate

In the same way as in example 3, title product was synthesized from potassium benzyl penicillinate (7.45 g, 0.02 mole) and p-nitrophenylchloromethyl carbonate (4.6 g, 0.02 mole) in 20 ml of dimethylsulphoxide. The product was obtained as 4.2 g of a brown heavy oil. The product showed strong IR absorbtion at 1780–1750 cm$^{-1}$ due to β-lactam and ester carbonyls. The product was rapidly hydrolysed in presence of human serum.

EXAMPLE 15.

β-Nitroethoxycarbonyloxymethyl m-F-α-azidobenzylpenicillinate

In the same way as in example 10 title product was synthesized from sodium m-F-α-azidobenzylpenicillinate (8.3 g, 0.02 mole) and p-nitroethylchloromethylcarbonate (2.5 g, 0.013 mole) in 25 ml of dimethylsulphoxide. The product was obtained as 0.4 g of a light brown oil. The product showed strong IR absorbtion at 2130 cm$^{-1}$ due to azido group and at 1780–1750 cm$^{-1}$ due to β-lactam and ester carbonyls. The product was rapidly hydrolyzed in presence of human serum.

EXAMPLE 16.

Phenoxycarbonyloxymethyl-m-F-α-azidobenzylpenicillinate

To an icecooled, stirred solution of tetrabutylammonium hydrogen sulphate (6.8 g, 0.02 mole) in 20 ml of 1M sodium hydroxide solution (0.02 mole) was added 20 ml of methylene chloride and sodium m-F-α-azidobenzylpenicillinate (8.3 g, 0,02 mole). The mixture was shaken and the layers were separated. To the organic solution was added phenyl-chloromethylcarbonate (3.72 g, 0.02 mole) and the solution was stirred at 40°C over night. The solution was poured into 80 ml of ice water and was extracted with 80+40 ml of ether. The combined organic extracts were washed with sodiumbicarbonate solution, water and brine, dried and evaporated in vacuo at 30°C to give 6.7 g of a green oil. The product was repeatedly washed with petroleum ether to remove phenyl-chloromethylcarbonate, dissolved in toluene and evaporated in vacuo at 30°C to give title product as 6.0 g of a green heavy oil. The product showed strong IR absorbtion at 2130 cm$^{-1}$ due to azido group and 1790–1750 cm$^{-1}$ due to β-lactam and estercarbonyls. The product was rapidly hydrolyzed in presence of human serum. NMR (CDCl$_3$, tetramethylsilane as internal standard) = 1.45–1.65 (d), 4.50 (s), 5.05 (s), 5.50–5.90 (m) 6.80–7.30 (m) ppm.

EXAMPLE 17.

Phenoxycarbonyloxymethylbenzylpenicillinate

To an icecooled suspension of potassium benzylpenicillinate (2.7 g, 0.007 mole) in 7 ml of dimethylformamide was added phenylchloromethyl carbonate (1.34 g, 0.007 mole) in 3.5 ml of dimethylformamide during 15 minutes. The suspension was stirred at room temperature for 17 hours, was then poured into 60 ml of icecooled sodium bicarbonate solution and extracted with 2×50 ml of ether. The combined organic extracts were washed with water and brine, dried and evaporated in vacuo at 30°C. The resulting oil was washed repeatedly with petroleum ether, dissolved in toluene and evaporated to give title product as 2.2 g of a yellowish gum.

The product showed strong IR absorbtion at 1790–1750 cm$^{-1}$ due to β-lactam and ester carbonyls. The product was rapidly hydrolyzed in presence of human serum. NMR (CDCl$_3$, tetramethylsilane as internal standard) = 1.48 (s), 3.60 (s), 4.42 (s), 5.40–5.90 (m), 6.15–6.35 (d), 7.00–7.50 (m) ppm.

EXAMPLE 18.

1'-Cyclopentoxycarbonyloxyethyl-6(2-phenylthiazolyl-4-acetamido)penicillinate

In the same way as in example 16 title product was synthesized from sodium 6-(2-phenylthiazolyl-4-acetamido)penicillinate (1.0 g, 0.0022 mole) and α-chloroethylcyclopentylcarbonate (0.42 g, 0.022 mole). The product was obtained as 250 mg of a yellow heavy oil. IR spectrum showed strong absorbtion at 1780–1740 cm$^{-1}$ due to β-lactam and ester carbonyls.

EXAMPLE 19.

β-Azidoethoxycarbonyloxymethyl-α-hydroxy benzyl penicillinate

In the same way as in example 3, title product was synthesized from sodium α-hydroxybenzylpenicillinate (3.7 g, 0.01 mole) and β-azidoethyl-chloromethyl carbonate (1.8 g, 0.01 mole). The product was obtained as a yellowish oil (2,51 g). IR spectrum showed strong absorbtion at 2130 cm$^{-1}$ due to azido group and at 1790–1750 cm$^{-1}$ due to β-lactam and ester carbonyls.

EXAMPLE 20.

β-Aminoethoxycarbonyloxymethyl-α-hydroxybenzylpenicillinate

β-Azidoethoxycarbonyloxymethyl-α-hydroxybenzylpenicillinate (1.4 g, 0.0028 mole) was hydrogenated at normal pressure and temperature for 2 hours with 2 g of 5 % palladium on carbon prehydrogenated catalyst and with 50 ml of ethylacetate as solvent. The mixture was filtered and the filtrate was washed with sodium bicarbonate solution, water and brine, dried and evaporated in vacuo to give title product as a yellowish oil (0.7 g).

IR spectrum showed no band at 2130 cm$^{-1}$ due to hydrogenation of azido group. IR showed strong absorbtion at 1790–1750 cm$^{-1}$ due to β-lactam and ester carbonyls.

EXAMPLE 21.

1'-p-Methoxyphenoxycarbonyloxymethyl 6-(D-α-azido-m-fluoro-phenylacetamido)penicillanate To a stirred ice-cooled suspension of sodium 6-(D-α-azido-m-fluoro-phenylacetamido)penicillinate (3.0 g, 0.007 mole) in dimethylformamide (10 ml) was added a solution of chloromethyl-p-methoxyphenylcarbonate (2 g) in dimethylformamide (5 ml). After stirring at room temperature for 15 hours the mixture was poured into saturated sodium bicarbonate. The inorganic solid was filtered off and washed with ether. The filtrate was extracted with ether. The ether extract was washed with water and brine, dried and evaporated in vacuo at 30°C to give 1'-p-methoxyphenoxycarbonyloxymethyl 6-(D-α-azido-m-fluoro-phenylacetamido)penicillinate as a dark reddish oil (2.3 g).

The product showed strong absorption at 2120 cm$^{-1}$ and 1785–1750 cm$^{-1}$ due to the azido group and β-lactam and ester carbonyls respectively and was found to be rapidly hydrolyzed to 6-(D-α-azido-m-fluoro-phenylacetamido)penicillanic acid in presence of human serum.

EXAMPLE 22.

1'-Ethoxycarbonyloxyethyl-6-aminopenicillinate

A. 1'-Ethoxycarbonyloxyethylbenzylpenicillinate (9.45 g, 0.021 mole) was dissolved in 75 ml of methylenechloride under argon-atmosphere. Quinoline (5.44 ml, 0.047 mole) was added and the stirred solution was chilled to −15°C. Phosphorus pentachloride (5.00 g, 0.024 mole) was added over a period of 2 minutes. Stirring at −10°C for 65 minutes before n-propylalkohol (15.7 g, 0.21 mole) was added during 5 minutes at −25°C. Stirring at −10°C for 30 minutes 7.5 g of sodium chloride dissolved in 33 ml of water was added and the temperature rose to 0°C. Stirring at 0°C for 30 minutes. pH was adjusted to 7.0 during half an hours adding of 2N sodium hydroxide at 0°C. The layers were separated and the water solution was extracted with 2×40 ml of methylene chloride. The combined organic extracts were washed with sodium bicarbonate solution, water and brine, dried and evaporated in vacuo to give 7.9 g of 1'-ethoxycarbonyloxyethyl-6-aminopenicillinate as a yellow gum. The product showed strong IR absorbtion at 1790–1750 cm$^{-1}$ due to β-lactam and ester carbonyls. The product showed no IR absorbtion at 1670 cm$^{-1}$ due to hydrolyses of amide group of the original benzylpenicillin.

1'-Ethoxycarbonyloxyethyl-5-methyl-3-(2-chlorophenyl)-4-isoxazolyl penicillinate B. 1-Ethoxycarbonyloxyethyl-6-aminopenicillinate (2.3 g, 0.007 mole) was dissolved in 35 ml of methylisobutyl ketone and 70 ml of water. 5-Methyl-3-(2-chlorophenyl)-4-isoxazolyl chloride (1.8 g, 0.007 mole) dissolved in 15 ml of methylene chloride was added during 15 minutes, keeping pH at 3.0 with autotitrator. Stirring for 20 minutes more, with pH control. Separation. The water was extracted with 2×10 ml of methylisobutyl ketone. The combined organic extracts were washed with water, sodiumbicarbonate solution, water and brine, dried and evaporated in vacuo to give title product as 3.7 g of a brownish heavy oil. The product showed strong IR absorbtion at 1790–1750 cm$^{-1}$ due to β-lactam and ester carbonyls.

EXAMPLE 23.

1'-Ethoxycarbonyloxyethyl-α-hydroxybenzylpenicillinate

In the same way as in example 22, title product was synthesized from 1'-ethoxycarbonyloxyethylbenzylpenicillinate via 1'-ethoxycarbonyloxyethyl-6-aminopenicillinate (2.3 g, 0.007 mole) and α-dichloroacetoxyphenylacetyl chloride (2.0 g, 0.007 mole). The sodium hydroxide consumption showed almost immediate hydrolyses of the dichloroacetyl-protecting group. 1'-Ethoxycarbonyloxyethyl-α-hydroxybenzylpenicillinate was obtained as 2.9 g of a yellowish heavy oil. The product showed the same IR absorbtion as the product of example 12.

EXAMPLE 24.

(Diethylamino)-ethoxycarbonyloxymethyl-6-(D-α-azidophenylacetamido)-penicillinate hydrochloride To a stirred icecooled suspension of potassium D-α-azidobenzylpenicillinate (10.3 g, 0.025 mole) in dimethyl formamide (30 ml) was added chloromethyldiethylaminoethylcarbonate hydrochloride (6.2 g, 0.025 mole) during 30 minutes. After stirring at room temperature for 15 hours the mixture was poured into 250 ml of saturated sodium bicarbonate solution and 100 ml of ether. The inorganic solid was filtered off and washed with ether. The water layer was extracted with ether. The combined ether extracts were washed with water, sodium bicarbonate and brine. The ether solution was then extracted with 150+100 ml of water at pH = 2.8. The combined water extracts were freezedried to give 0.8 g of (diethylamino)-ethoxycarbonyloxymethyl-6-(D-α-azido-phenlacetamido) penicillinate hydrochloride as a yellow amorphous solid. The product showed strong IR absorbtion at 2130 cm$^{-1}$ due to azido group and at 1790–1750 cm$^{-1}$ due to β-lactam and ester carbonyls. The product was rapidly hydrolysed in presence of human serum.

EXAMPLE 25.

(Diethylamino)-ethoxycarbonyloxy-methyl-benzyl-penicillinate

In the same way as in example 16, title product was synthesized from potassium benzylpenicillinate (3.7 g, 0.01 mole) and (diethylamino)-ethylchloromethylcarbonate, freshly generated from its hydrochloride (2.5 g, 0.01 mole), but was extracted with ethylacetate instead of ether. Title product was obtained as 1.3 g of a yellowish gum. The product showed strong IR absorbtion at 1780–1730 cm$^{-1}$ due to β-lactam and ester carbonyls. The product was rapidly hydrolyzed in presence of human serum.

EXAMPLE 26.

(Diethylamino)-ethoxycarbonyloxy-methyl-α-hydroxybenzylpenicillinate

In the same way as in example 25, title product was synthesized from sodium α-hydroxybenzylpenicillinate (3.7 g, 0.01 mole) and (diethylamino)-ethyl-chloromethylcarbonate. The product was obtained as 0.6 g of a yellow solid foam. The product showed strong IR absorbtion at 1780–1740 cm$^{-1}$ due to β-lactam and ester carbonyls.

EXAMPLE 27.

1'-Phenoxycarbonyloxymethyl benzylpenicillinate

To a stirred, ice-cooled suspension of potassium benzylpenicillinate (26.8 g, 0.07 mole) in dimethyl formamide (70 ml) was added a solution of chloromethyl-phenylcarbonate (13.4 g, 0.07 mole) in dimethylformamide (35 ml), during 30 minutes. After stirring at room temperature for 17 hours the mixture was poured into 0.5 l of saturated sodium bicarbonate. To this mixture was added ether and water until no solid was left in the aqueous phase, which was then extracted with more ether. The combined organic extracts were washed with water and brine, dried and evaporated in vacuo at 30°C. The oily residue was washed repeatedly by decantation with petroleum ether to remove nonreacted chloromethylethylcarbonate. The resulting oil was dissolved in toluene and evaporated to a reddish gum. (22.1 g). The product showed strong IR absorption at 1785–1750 cm$^{-1}$ due to β-lactam and ester carbonyls and was rapidly hydrolyzed in presence of human serum.

EXAMPLE 28.

(Diethylamino)-ethoxycarbonyloxymethyl 6-(D-αazido-phenylacetamido)penicillinate To a stirred ice-cooled suspension of potassium D-α-azido-benzylpenicillinate (4.1 g, 0.01 mole) in dimethylformamide (10 ml) was added chloromethyldiethylaminoethylcarbonate hydrochloride (2.5 g during 30 minutes. After stirring at room remperature for 15 hours the mixture was poured into 3 l of saturated potassium carbonate. The inorganic solid was filtered off and washed with ether. The filtrate was extracted with ether. The ether extract was washed with water and sodium bicarbonate and brine, dried and evaporated in vacuo at 30°C to give diethylamino-ethoxycarbonyloxymethyl 6-(D-α-azido-phenylacetamido)-penicillinate as a reddish gum (3.7 g). The product showed strong IR absorbtion at 2120 cm$^{-1}$ and 1785–1750 cm$^{-1}$ due to the azido group and β-lactam and ester carbonyls respectively and was found to be rapidly hydrolyzed to 6-D(-α-azidophenylacetamido) penicillanic acid by human serum.

EXAMPLE 29.

Pharmaceutical formulations

For preparation of tablets the following compositions were made:

| a) | β-Aminoethoxycarbonyloxymethyl 6-phenylacetamido penicillinate | 300 mg |
| | Starch | 100 mg |
| | Magnesium stearate | 10 mg |
| b) | Ethoxycarbonyloxymethyl 6-(2-phenylthiazolyl-4-acetamido)penicillinate | 350 mg |
| | Starch | 100 mg |
| | Magnesium stearate | 10 mg |
| c) | Ethoxycarbonyloxymethyl 6(3-pyridylacetamido) penicillinate hydrochloride | 350 mg |
| | Calcium carbonate | 100 mg |
| | Magnesium stearate | 10 mg |
| d) | Ethoxycarbonyloxymethyl 6-phenoxyacetamido penicillinate hydrochloride | 400 mg |
| | Lactose | 100 mg |
| | Magnesium stearate | 10 mg |
| e) | Phenoxycarbonyloxymethyl 6-(2-phenylthiadiazolyl-5-acetamido)penicillinate | 370 mg |
| | Microcrystalline cellulose (Avicel) | 100 mg |
| | Magnesium stearate | 10 mg |
| f) | 1'-Ethoxycarbonyloxyethyl 6-(D-α-hydroxyphenyl acetamido)penicillinate | 338 mg |
| | Calcium carbonate | 100 mg |
| | Lactose | 100 mg |
| | Magnesium stearate | 10 mg |

For filling in capsules the following formulations were made:

| g) | Ethoxycarbonyloxymethyl 6-(2,6-dimethoxybenzamdio) penicillinate | 350 mg |
| | Magnesium stearate | 5 mg |
| h) | 1'-Ethoxycarbonyloxyethyl 6-(D-α-hydroxyphenyl-acetamido)penicillinate hydrochloride | 350 mg |
| | Lactose | 40 mg |
| | Magnesium stearate | 5 mg |

For oral suspensions the following formulations were prepared:

| i) | Ethoxycarbonyloxymethyl 6-(3-pyridylacetamido)-penicillinate hydrochloride | 36 | g |
| | Sodium benzoate | 0.48 | g |
| | Sodium chloride | 0.75 | g |

| | | |
|---|---|---|
| Flavouring agents | 4.7 | g |
| Aerosil | 0.3 | g |
| Antifoam | 0.0375 | g |
| Alkali salts of polysaccharide sulphates | 4.0 | g |
| Sodium saccharinate | 0.4 | g |
| Sorbitol | ad 100 | g |

We claim:

1. A method for treatment of bacterial infection in a mammal comprising oral administration to said mammal of an anti-bacterially effective amount of a pharmaceutical composition containing, as an active ingredient in a pharmaceutically acceptable carrier, at least 1% (w/w) of a carbonate ester of the structural formula

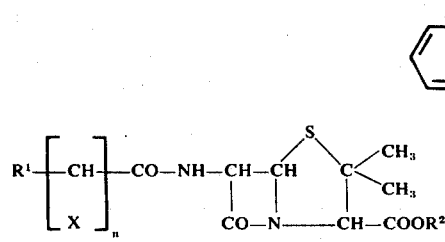

(I)

or a therapeutically acceptable salt thereof, in which formula $R^1$ is phenyl which may be unsubstituted or substituted with one or more members of the group consisting of amino, alkyl groups containing from 1 to 4 carbon atoms, halogen, and phenyl; $R^2$ represents the group

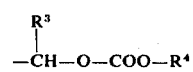

in which formula $R^3$ is selected from the group consisting of hydrogen and methyl, and $R^4$ is selected from the group consisting of alkyl groups containing from 1 to 8 carbon atoms, cycloalkyl groups containing from 3 to 7 carbon atoms, benzyl, and phenyl, whereby the alkyl, cycloalkyl, benzyl, and phenyl groups may be unsubstituted or substituted with one or more groups selected from the class consisting of amino, methylamino, diethylamino, and nitro; X is selected from the group consisting of hydrogen and hydroxy; and $n$ is 0 or 1, provided that X is hydroxy when n is 1 and $R^4$ is an unsubstituted alkyl group.

2. The method according to claim 1 wherein the active ingredient of the composition is a carbonate ester of the formula

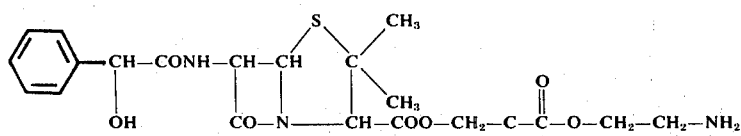

3. The method according to claim 1 wherein the active ingredient of the composition is a carbonate ester of the formula

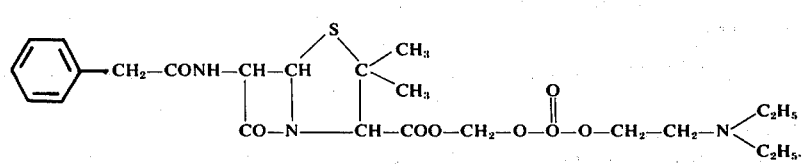

4. The method according to claim 1 wherein the active ingredient of the composition is a carbonate ester of the formula

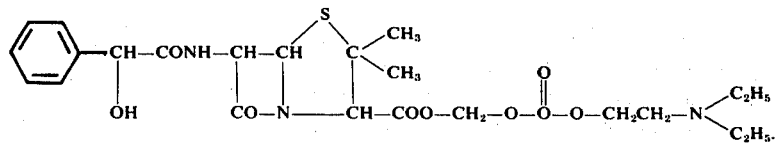

5. The method, according to claim 1 wherein the active ingredient of the composition is a carbonate ester of formula I, wherein $R^1$, $R^2$, $R^3$, X, and n have the meaning given in claim 30, and wherein $R^4$ is selected from the group consisting of ethyl, benzyl, and phenyl, whereby the ethyl, benzyl, and phenyl groups may be unsubstituted or substituted with a group selected from the class consisting of amino, diethylamino, and nitro groups.

6. The method according to claim 1 wherein the active ingredient of the composition is a carbonate ester of formula I, wherein the group

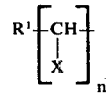

is selected from the class consisting of benzyl, α-hydroxybenzyl, and p-aminobenzyl, and wherein $R^2$, $R^3$, and $R^4$ have the meaning given in claim 1.

7. The method according to claim 1 wherein the active ingredient of the composition is a carbonate ester of the formula

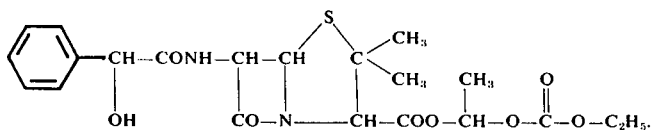

8. A pharmaceutical composition for the treatment of bacterial infection in a mammal which comprises as the active ingredient an anti-bacterially effective amount of a carbonate ester of the structural formula

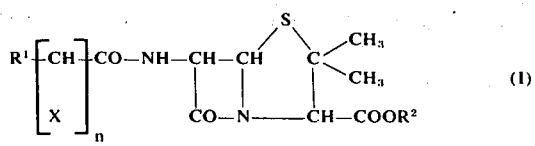

or a therapeutically acceptable salt thereof, in which formula $R^1$ is phenyl which may be unsubstituted or substituted with one or more members of the group consisting of amino, alkyl groups containing from 1 to 4 carbon atoms, halogen, and phenyl; $R^2$ represents the group $$-\overset{R^3}{\underset{|}{C}H}-O-COO-R^4$$

in which formula $R^3$ is selected from the group consisting of hydrogen and methyl, and $R^4$ is selected from the group consisting of alkyl groups containing from 1 to 8 carbon atoms, cycloalkyl groups containing from 3 to 7 carbon atoms, benzyl, and phenyl, whereby the alkyl, cycloalkyl, benzyl, and phenyl groups may be unsubstituted or substituted with one or more groups selected from the class consisting of amino, methylamino diethylamino, and nitro; X is selected from the group consisting of hydrogen and hydroxy; and n is 0 or 1, provided that X is hydroxy when n is 1 and $R^4$ is an unsubstituted alkyl group in a pharmaceutically acceptable carrier.

9. The pharmaceutical composition according to claim 8 wherein the active ingredient of the composition is a carbonate ester of formula I wherein $R^1$, $R^2$, $R^3$, X and n have the meaning given in claim 8 wherein $R^4$ is selected from the group consisting of ethyl, benzyl, and phenyl, whereby the ethyl, benzyl, and phenyl groups may be unsubstituted or substituted with a group selected from the class consisting of amino, diethylamino, and nitro groups.

10. The pharmaceutical composition according to claim 8 wherein the active ingredient of the composition is a carbonate ester of formula I, wherein the group

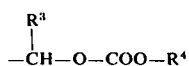

is selected from the class consisting of benzyl, α-hydroxybenzyl, and p-aminobenzyl, and wherein $R^2$, $R^3$, and $R^4$ have the meaning given in claim 8.

11. The pharmaceutical composition according to claim 8 wherein the active ingredient is a carbonate ester of the formula

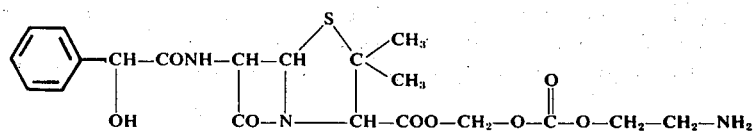

or a therapeutically acceptable salt thereof.

12. The pharmaceutical composition according to claim 8 wherein the active ingredient is a carbonate ester of the formula

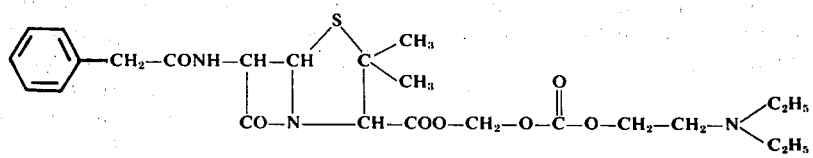

or a therapeutically acceptable salt thereof.

13. The pharmaceutical composition according to claim 8 wherein the active ingredient is a carbonate ester of the formula

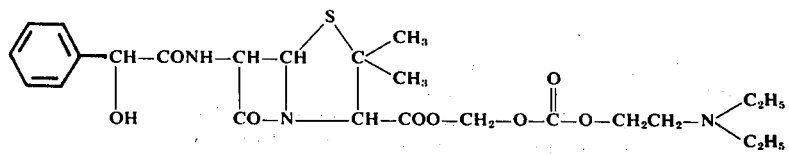

or a therapeutically acceptable salt thereof.

14. The pharmaceutical composition according to claim 8 wherein the active ingredient is a carbonate ester of the formula

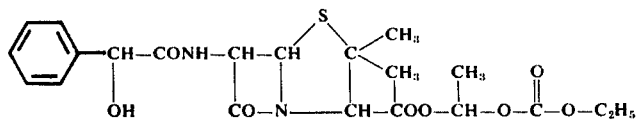
or a therapeutically acceptable salt thereof.